(12) United States Patent
Kuipers

(10) Patent No.: US 9,891,195 B2
(45) Date of Patent: Feb. 13, 2018

(54) METHOD FOR THE PRODUCTION OF A FLAME IONIZATION DETECTOR AND CORRESPONDING FLAME IONIZATION DETECTOR

(71) Applicant: KROHNE Messtechnik GmbH, Duisburg (DE)

(72) Inventor: Winfried Kuipers, Essen (DE)

(73) Assignee: KROHNE Messtechnik GmbH, Duisburg (DE)

( * ) Notice: Subject to any disclaimer, the term of this patent is extended or adjusted under 35 U.S.C. 154(b) by 1161 days.

(21) Appl. No.: 13/680,400

(22) Filed: Nov. 19, 2012

(65) Prior Publication Data

US 2014/0035593 A1     Feb. 6, 2014

(30) Foreign Application Priority Data

Aug. 3, 2012 (DE) .......................... 10 2012 015 204

(51) Int. Cl.
| | | |
|---|---|---|
| *C03B 29/00* | (2006.01) | |
| *B32B 37/00* | (2006.01) | |
| *G01N 27/62* | (2006.01) | |
| *C04B 37/00* | (2006.01) | |

(Continued)

(52) U.S. Cl.
CPC ......... *G01N 27/626* (2013.01); *C04B 37/001* (2013.01); *G01N 30/68* (2013.01); *C04B 2237/32* (2013.01); *C04B 2237/62* (2013.01); *G01N 30/6095* (2013.01)

(58) Field of Classification Search
CPC .... G01N 27/626; G01N 27/62; C04B 37/001; C04B 2237/32; C04B 2237/61
See application file for complete search history.

(56) References Cited

U.S. PATENT DOCUMENTS 3,095,278 A * 6/1963 Green, Jr. ............ G01N 27/626
422/54
5,969,617 A   10/1999 Garthe
(Continued)

FOREIGN PATENT DOCUMENTS

DE    44 25 304 A1    2/1996
DE    102 47 857 A1   4/2004
(Continued)

OTHER PUBLICATIONS

Kuipers et al. "A planar micro-flame ionization detector with an integrated guard electrode", J. Micromech. Microeng., vol. 18, pp. 1-7, published May 15, 2008.*
(Continued)

*Primary Examiner* — Alex Efta
(74) *Attorney, Agent, or Firm* — David S. Safran

(57) ABSTRACT

A flame ionization detector having at least one combustion chamber, at least one conduit for directing a gas or gas mixture, and at least one electrode structure, and a process for forming the flame ionization detector by providing two or more green ceramic films, forming geometric structures in said green ceramic films, depositing at least a portion of an electrically conductive structure on at least one of said green ceramic films, stacking said green ceramic films, laminating said green ceramic films, and sintering said laminated green ceramic films to form said flame ionization detector.

12 Claims, 3 Drawing Sheets

(51) Int. Cl.
*G01N 30/68* (2006.01)
*G01N 30/60* (2006.01)

(56) References Cited

U.S. PATENT DOCUMENTS

| | | | |
|---|---|---|---|
| 6,592,696 B1* | 7/2003 | Burdon | B01J 19/0093 |
| | | | 156/219 |
| 6,666,907 B1* | 12/2003 | Manginell | G01N 30/6095 |
| | | | 73/23.36 |
| 8,305,086 B2 | 11/2012 | Jörg et al. | |
| 2003/0118481 A1* | 6/2003 | Briscoe | F04B 19/006 |
| | | | 422/89 |
| 2004/0043479 A1 | 3/2004 | Briscoe et al. | |
| 2010/0301870 A1* | 12/2010 | Muller | G01N 30/68 |
| | | | 324/464 |
| 2012/0141946 A1 | 6/2012 | Müller et al. | |

FOREIGN PATENT DOCUMENTS

| | | |
|---|---|---|
| DE | 10 2009 035 762 A1 | 2/2011 |
| EP | 2 447 716 A1 | 5/2012 |
| GB | 1 451 795 A | 10/1976 |
| WO | 2009/036854 A1 | 3/2009 |

OTHER PUBLICATIONS

Bae et al. "Development of a portable gas analyzer using a micro-Gas Chromatograph/Flame Ionization Detector (micro-GC/FID) for NASA's environmental missions", 42nd Internation Coverence on Environmental Systems, Jul. 15-19, 2012, San Diego, California.*

Bae et al. "Development of a portable gas analyzer using a micro-Gas Chromatograph/Flame Ionization Detector (micro-GC/FID) for NASA's environmental missions", 42nd International Coverence on Environmental Systems, Jul. 15-19, 2012, San Diego, California.*

Ming-Hsun Wu and Richard A. Yetter, Development and Analysis of a LTCC Micro Stagnation-Point Flow Comubstor, Jurnal of Micromechanics and Microengineering, vol. 18, 2008, No. 12,125016, p. 1-9, ISSN 0960-1317.

* cited by examiner

# METHOD FOR THE PRODUCTION OF A FLAME IONIZATION DETECTOR AND CORRESPONDING FLAME IONIZATION DETECTOR

BACKGROUND OF THE INVENTION

Field of the Invention

The invention relates to a method for the production of a flame ionization detector, whereby the flame ionization detector has at least one combustion chamber, at least one channel for directing a gas or gas mixture, and at least one electrode structure. The invention also relates to a corresponding flame ionization detector.

Description of Related Art

Flame ionization detectors (FID) are used for the measurement of organic compounds, in particular volatile hydrocarbon-containing substances. The principle of operation consists in that the electrical conductivity of an oxy/hydrogen flame between two electrodes is measured. The medium that is to be analyzed is in this case directed into a combustion space with a combustion gas (usually hydrogen gas or a mixture of hydrogen and helium) and an oxidizing agent (in most cases oxygen or air) and ionized there. The ions are detected by a voltage being applied to two electrodes (measuring electrode and counter-electrode), which are arranged in the area of the combustion chamber, and the ion stream that is produced is measured and evaluated.

One advantage of the flame ionization detectors consists in the fact that the measurement signal over a wide concentration range is linearly proportional to the amount of the analytes, or more precisely to their hydrogen-bound carbon content. Therefore, for example, the concentration of a hydrocarbon can be determined without prior calibration.

A flame ionization detector usually has a combustion chamber, electrodes, channels for feeding in and drawing off gases or gas mixtures, and an ignition device. The openings of the channels into the combustion chamber are referred to as nozzles. In order to prevent leakage currents flowing through the system from being co-detected and thus distorting the measurement, in most cases a protective electrode is also provided.

If the combustion gas and the oxidizing agent are directed into the combustion chamber from opposite directions, the arrangement is also referred to as a counter-current burner. Counter-current flames burn in the immediate vicinity of a stagnation point, which because of the minimal heat loss accounts for the high ionization efficiency of such flames.

Since hydrogen is used in the measurement, flame ionization detectors are preferably configured to be small, so as to reduce the risk of explosion. Such a miniaturized flame ionization detector is referred-to as a µFID.

Flame ionization detectors that are produced with the method of the microsystem technique are known. The International Patent Application Publication WO 2009/036854 A1 or the related European Patent EP 2 191 263 B1 and corresponding U.S. Patent Application Publication 2010/0301870 A1, describe a flame ionization detector that is designed to be planar and that consists of at least three small plate-like substrates that consist of glass or silicon and that are connected to one another.

The German Patent Application DE 10 2009 035 762 A1 and European Patent Application EP 2 447 716 A1 describe a flame ionization detector that also consists of three layers (glass or silicon) and that is manufactured by means of the method of the microsystem technique, and said flame ionization detector is configured as a counter-current burner.

The measuring and protective electrodes are applied in a thin-film technique to the bottom of a substrate, whereby the side walls of the combustion chamber form the counter-electrode. Moreover, a temperature-dependent resistor is also provided as a temperature sensor. Different arrangements of the channels for the directing of gases are discussed. Based on the fact that substrates that consist of different materials are used with temperature coefficients that are different to some extent, the detector can be adversely affected by thermal stress depending on the application, or the structures of the detector can be configured based on different expansion behavior as a result of temperature changes.

In the article "Development and Analysis of a LTCC Micro Stagnation-Point Flow Combustor" by Ming-Hsun Wu and Richard A. Yetter, J. Micromech. Microenc. 18 (2008), Number 12, a counter-current burner is described, which was produced by means of an LTCC method.

Low-temperature co-fired ceramics (LTCC) are used to produce multi-layer ceramic structures. In this case, unfired, so-called "green" ceramic films are structured individually, stacked, laminated, and subjected to a sintering profile at a peak temperature of approximately 850° C.-900° C.; below, the technical term "green ceramic films" is used to describe unfired ceramic films. At the maximum temperatures that occur during sintering, the LTCC method is distinguished from the production of high-temperature co-fired ceramics (High-Temperature Co-Fired Ceramics, HTCC), which are sintered at temperatures of between 1600° C. and 1800° C. In addition, thick-layer hybrid techniques are known, whereby strip conductors or resistors are applied using the silk-screen method on already-sintered ceramic substrates. The printed carrier is fired, whereby the applied pastes fuse to the layers. Subsequently, assembly of the discrete components takes place.

SUMMARY OF THE INVENTION

The object of the invention is a method for the production of a µFID, which avoids the drawbacks of the prior art and results in a µFID, which has in particular a high resistance relative to the conditions in the combustion chamber, such as, for example, reactive oxygen at high temperature.

The method according to the invention, in which the previously deduced and indicated object is achieved, is characterized first and essentially by the following steps: geometric or spatial structures, in the form of through-recesses and/or cavities, are introduced in relatively thin layered green ceramic films. As an alternative or in addition, green ceramic films with already existing geometric or spatial structures, in particular also preferably in the form of through-recesses and/or cavities, are produced, such that the green ceramic films already have the geometric or spatial structures after their production. In another step, at least one part of an electrically conductive structure (for example, by means of a silk-screen method) is applied to at least one green ceramic film. In one configuration, the electrically conductive structure is formed at least partially by a metal structure. Parts of the electrically conductive structure are, for example, a conductor structure for an electrical contact and/or at least one portion of the electrode structure (at least a measuring electrode and a counter-electrode, preferably supplemented by at least one protective electrode). The green ceramic films which form the flame ionization detector are stacked on one another in the next step. In this case, the green ceramic films may have already been previously grouped into blocks or several ceramic films may have been packed into thicker ceramic film stacks in advance. Then, the stacked green ceramic films are laminated with one another. Subsequently, the green ceramic films are subjected to a sintering process. The sintered stack can optionally be machine-finished. Thus, for example, electrical contacts or fluid or thermal supply and/or discharge conduits are also attached or mounted. After sintering, an essentially ceramic monolith is produced, which is distinguished in particular in that it is hermetically sealed except for the deliberately introduced through-holes and channels, and its components do not show any differing thermal expansion behavior, so that no thermal stress is produced as a result of a temperature change. In addition, high temperature stability is produced by the sintering process. Relative to certain chemicals, the sintered ceramic layers are also considerably more resistant than, for example, layers that consist of silicon or glass. The number of used and optionally grouped ceramic layers in this case can be very high, in particular greater than 10, for example up to 28.

In one configuration, the green ceramic films are subjected to a sintering process with a maximum temperature of below 1000° C. (in particular, between 800° C. and 900° C.). According to this configuration, essentially an LTCC method for producing a μFID is used.

In an alternative configuration, the green ceramic films are subjected to a sintering process with a maximum temperature of above 1000° C. (in particular between 1600° C. and 1800° C.). According to this configuration, essentially an HTCC method for the production of a μFID is used, which ensures still higher chemical and thermal resistance.

In one configuration, (geometric) structures are introduced into the green ceramic films, or the green ceramic films are produced with structures in such a way that structures in different ceramic films are combined to form at least one hollow space. This follows on to structures that run in only one film or a uniform block of films and that already form a hollow space there. In this case, the hollow space can be, e.g., the combustion chamber, a channel, or fluid supply conduit, etc. This configuration takes into account the fact that the sizing of the necessary overall structures of the FID can be larger than the thicknesses of the individual ceramic films. Therefore, the ceramic films are structured in such a way that, when stacked, they are mutually combined to form the hollow spaces of the FID. The structuring in this case is done on individual ceramic films or on ceramic films that are stacked to form blocks.

In one configuration, in each case at least a portion of an electrically conductive structure (e.g., a conductor structure and/or at least a portion of the electrode structure) is applied on several ceramic films in such a way that the applied parts of the electrically conductive structure are mutually combined (for example, to form the complete sections of the conductor structure or the electrode structure, etc.). Also, in the case of the electrical structures, the components are combined on the ceramic films to form the necessary overall structures. Individual structures can optionally extend only over a single ceramic film.

To avoid the effect of leakage currents flowing through the system, at least one protective electrode is provided in a configuration. The following configurations relate to such a protective electrode.

In one configuration, it is provided that at least one essentially mesh-like protective electrode is applied on at least one green ceramic film. In particular after the process of the lamination, the ceramic film with the mesh-like protective electrode is located between the measuring electrode and the counter-electrode. In addition, optionally still other ceramic films are located between the ceramic film with the mesh-like protective electrode and the measuring electrode or between the ceramic film that is provided with the mesh-like protective electrode and the counter-electrode for the purpose of insulation.

In another configuration, at least a portion of the electrode structure is produced on a green ceramic film in such a way that a protective electrode is applied at least partially on the green ceramic film. An insulator (e.g., a dielectric paste) is applied at least partially on the protective electrode, and a measuring electrode is applied at least partially on said insulator. In another configuration, another insulator and another protective electrode follow the measuring electrode.

In addition, the invention relates to a flame ionization detector, which has been produced according to one of the previously mentioned configurations of the inventive method.

One configuration of the flame ionization detector calls for electrical and/or fluidic and/or thermal supply and/or discharge conduits to be at least partially concentrated on one side of the flame ionization detector so that the flame ionization detector allows use as a surface-mounted device (SMD) component. In this case, electrical supply and/or discharge conduits are electrical connections that are used, e.g., in picking up a sensor signal or for operating the electrode structure or a temperature sensor. The fluidic supply and/or discharge conduits are used, for example, in the supply of the measuring medium, the necessary gases, or for removing the exhaust gases. In this regard, fluid is therefore related to gaseous or liquid or other flowable media. Thermal supply and/or discharge conduits allow the removal of heat from the combustion chamber or a preheating of the measuring medium or the gases, etc. In this configuration, at least a portion of the supply and/or discharge conduits is concentrated on one side, e.g., on a lower side of the flame ionization detector, i.e., led to this side for connection to supply or drain lines or components, etc., so that the flame ionization detector preferably allows application as SMD components. Such surface-mounted devices allow the direct application on, for example, a conductor plate.

In particular, there are now a number of embodiments to configure and further develop the method according to the invention and the flame ionization detector according to the invention. To this end, reference is made to the claims and to the following detailed description of the invention, in connection with the drawings.

DETAILED DESCRIPTION OF THE INVENTION

Figure 1:
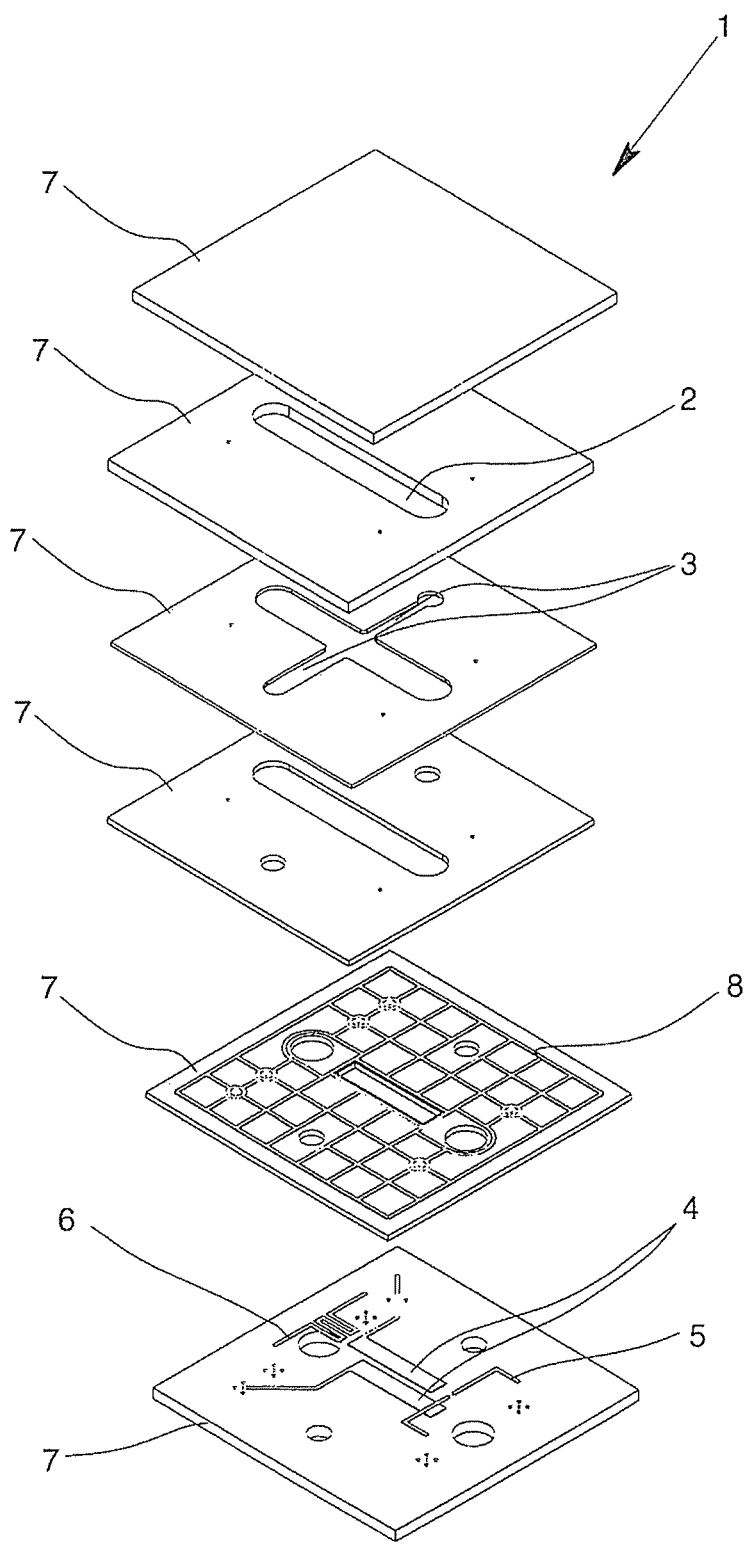
FIG. 1 shows a diagrammatic exploded view of a flame ionization detector according to the invention.

In an exploded view, FIG. 1 shows a flame ionization detector 1 that has six planes or six blocks and that is configured in particular as a μFID. The combustion chamber 2, in which the sample to be examined is ionized in a hydrogen flame, is located centrally. Channels 3 are used to supply combustion gas or oxidizing agent and then also to drain off the combustion gas, and said channels empty via so-called nozzles into the combustion chamber 2.

The ion stream is measured by the electrode structure 4 as part of the electrically conductive or in particular metal structure with a measuring electrode and a counter-electrode and in particular preferably also a protective electrode 8 by an electrical voltage being applied to the measuring electrode and the counter-electrode. The measured stream allows an assessment of the concentration of a certain substance in the medium that is to be examined.

For production of the flame, an ignition device 5 is also provided. In addition, the measurement uses a temperature sensor 6, which is shown here in the form of a meandering temperature-dependent resistor.

The flame ionization detector 1 consists of several blocks of single or multiple ceramic films 7, which in each case have a structure in the form of through-recesses or cavities, which when stacked are combined as a whole to form the hollow spaces that are necessary for the operation of the flame ionization detector 1. In addition, the necessary electrical structures, such as the electrode structure 4, the conductor structures that are necessary, for example, for directing the measurement signals, or else an essentially mesh-like protective electrode 8 are also provided on the ceramic films 7 or the blocks that are formed therefrom in each case. The electrically conductive structures preferably run inside the flame ionization detector 1 and provide through contacts for the connections, here directed downward in the figures. Preferably, all other supply conduits or discharge conduits for gases, liquids, electrical connections, thermal connections or lead-aways are also directed to one side or to one surface, here in particular to the bottom of the flame ionization detector 1. This allows the flame ionization detector 1 to be used, for example, as an SMD component and to be mounted directly on other structures.

As parts of the electrode structure 4, ignition device 5, temperature sensor 6, etc., the individual electrically conductive or metal structures, connections, through-recesses, measuring electrodes and counter-electrodes are depicted here all bundled above the bottommost block of the ceramic films 7 for clarity of depiction. In the depiction, this results in the mesh-like protective electrode 8 being arranged above the electrode structure 4 with measuring electrodes and counter-electrodes. For practical implementation, however, the protective electrode 8 can be located in a plane between the measuring electrode and the counter-electrode.

In one configuration (not depicted here) the counter-electrode, the temperature sensor 6 and/or the ignition device 5 are located below the topmost block, which is designed to be planar and without geometric structures. In this case the topmost block operates as a cover. On this cover, additional (not depicted here) components can optionally also be mounted, thus, e.g., a cooling unit.

Figure 2:
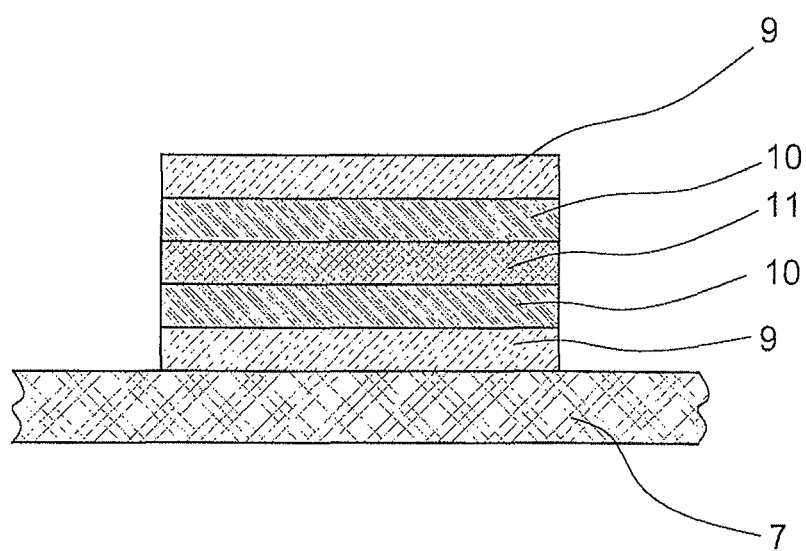
FIG. 2 shows a diagrammatic view of a portion of an electrode structure of a flame ionization detector according to the invention of an alternative configuration in section.

FIG. 2 shows a section through a pure diagrammatic arrangement of a configuration of the electrode structure 4 that is an alternative to FIG. 1. Shown primarily is the area of the protective electrode 9 that is designed as an alternative for a mesh-like protective electrode 8 of FIG. 1. A protective electrode 9, which is separated electrically from the measuring electrode 11 by an insulator 10 (e.g. a dielectric paste), is located on a ceramic film 7. Above the measuring electrode 11, there is another insulator 10 and consequently another protective electrode 9. The measuring electrode 11 is therefore completely surrounded by the protective electrode 9. For insulation, for example, a dielectric paste can also be applied, preferably even when turned on the sides.

Figure 3:
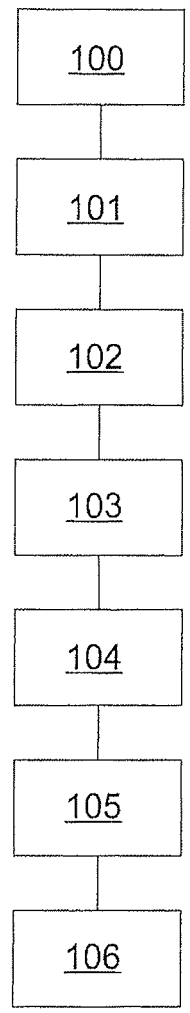
FIG. 3 shows a diagrammatic view of a time plot of the steps of the production method according to the invention of a flame ionization detector.

FIG. 3 indicates a sequence of the individual steps of the method according to the invention.

In Step 100, individual green ceramic films or blocks 7 are arranged in groups or stacks. In Step 101, structures are generated in groups, e.g., by punching, milling or etching. Thus, the geometries that when combined as a whole form conduits for gases or for through-recesses, etc., in the finished flame ionization detector are introduced.

In Step 102, the electrical or in particular metal structures, elements, etc., are applied on the ceramic films. This, for example, can be at least partially accomplished by a silk-screening method.

In Step 103, the involved ceramic films/blocks are stacked, and in Step 104, they are laminated, in order to be subjected to a sintering process in Step 105.

In Step 106, a machine-finishing of the sintered ceramic monolith also takes place.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method for the production of a flame ionization detector having at least one combustion chamber, at least one channel forming a fluidic supply and discharge conduit for directing a gas or gas mixture, and at least one electrode structure forming an electric supply, and having at least one thermal supply and discharge conduit, comprising the steps of:
   providing two or more green ceramic films;
   forming geometric structures in said green ceramic films;
   depositing at least a portion of an electrically conductive structure on at least one of said green ceramic films;
   stacking said green ceramic films;
   laminating said green ceramic films; and
   sintering said laminated green ceramic films to form said flame ionization detector;
   arranging all of the electric supply, and the fluidic, and thermal supply and discharge conduits in the flame ionization detector concentrated on one side of the flame ionization detector so that the flame ionization detector is a surface mounted device (SMD).

2. The method according to claim 1, wherein the geometric structures formed in the green ceramic films form through-recesses and/or cavities in the stacked ceramic films.

3. The method according to claim 1, wherein the geometric structures are formed in the green ceramic films in such a way that, when the green ceramic films are stacked, the geometric structures combine in the different ceramic films to form at least one hollow space.

4. The method according to claim 1, wherein at least a portion of the electrically conductive structure is applied by a silk-screening method.

5. The method according to claim 1, wherein sintering is conducted at a maximum temperature of below about 1000° C.

6. The method according to claim 1, wherein sintering is conducted at a temperature between about 800° C. and about 900° C.

7. The method according to claim 1, wherein sintering is conducted at a maximum temperature of above about 1000° C.

8. The method according to claim 1, wherein sintering is conducted at a temperature between about 1600° C. and about 1800° C.

9. The method according to claim 1, wherein the electrically conductive structure is applied on several green ceramic films in such a way that applied parts of the electrically conductive structure are mutually combined.

10. The method according to claim 1, further comprising machine-finishing the sintered ceramic films of the flame ionization detector.

11. The method according to claim 1, further comprising applying at least one protective electrode in the form of a mesh on at least one green ceramic film.

12. The method according to claim 1, wherein said electrically conductive structure comprises at least one protective electrode and at least one measuring electrode, separated by at least one insulator material.

* * * * *